United States Patent
Mordaunt et al.

(10) Patent No.: US 9,216,066 B2
(45) Date of Patent: Dec. 22, 2015

(54) SYSTEM AND METHOD FOR CREATING A CUSTOMIZED ANATOMICAL MODEL OF AN EYE

(71) Applicants: Bausch & Lomb Incorporated, Rochester, NY (US); Technolas Perfect Vision GmbH, Munich (DE)

(72) Inventors: David Haydn Mordaunt, Los Gatos, CA (US); Holger Schlueter, Munich (DE); Frieder Loesel, Mannheim (DE)

(73) Assignees: BAUSCH & LOMB INCORPORATED, Rochester, NY (US); TECHNOLAS PERFECT VISION GMBH, Munich (DE)

( * ) Notice: Subject to any disclaimer, the term of this patent is extended or adjusted under 35 U.S.C. 154(b) by 187 days.

(21) Appl. No.: 13/792,931

(22) Filed: Mar. 11, 2013

(65) Prior Publication Data

US 2013/0294668 A1    Nov. 7, 2013

Related U.S. Application Data

(60) Provisional application No. 61/636,582, filed on Apr. 20, 2012.

(51) Int. Cl.
| | |
|---|---|
| G06K 9/00 | (2006.01) |
| A61B 19/00 | (2006.01) |
| A61B 3/00 | (2006.01) |
| A61B 3/117 | (2006.01) |

(52) U.S. Cl.
CPC ............... *A61B 19/50* (2013.01); *A61B 3/0025* (2013.01); *A61B 3/117* (2013.01)

(58) Field of Classification Search
None
See application file for complete search history.

(56) References Cited

U.S. PATENT DOCUMENTS

| | | |
|---|---|---|
| 3,169,459 A | 2/1965 | Friedberg |
| 4,881,808 A | 11/1989 | Bille et al. |
| 5,214,456 A | 5/1993 | Gersten |
| 5,246,435 A | 9/1993 | Bille et al. |
| 5,439,462 A | 8/1995 | Bille et al. |
| 6,275,718 B1 | 8/2001 | Lempert |
| 6,325,792 B1 | 12/2001 | Swinger et al. |
| 6,454,761 B1 | 9/2002 | Freedman |
| 6,579,282 B2 | 6/2003 | Bille et al. |

(Continued)

OTHER PUBLICATIONS

J.A. Izatt and M.A. Choma. "Theory of Optical Coherence Tomography" Springer, 1346 p. 758, ISBN: 978-3-540-77549-2. 2008.*

(Continued)

*Primary Examiner* — Bhavesh Mehta
*Assistant Examiner* — Oneal R Mistry
(74) *Attorney, Agent, or Firm* — Nydegger & Associates

(57) ABSTRACT

A system and method for creating a line recognition template that replicates an object is provided for use as a control reference during ophthalmic surgery on the object. Creation of the template first requires aligning a plurality of reference points along a central "z" axis, with anatomically measured lengths ($\Delta$"z"$_n$) between adjacent reference points. Axially-symmetric surfaces can then be traced between selected, adjacent, reference points to create the template. For the present invention, the location of reference points, and the tracing of axially-symmetric surfaces, are based on a cross sectional image of the object for surgery. Preferably, the cross sectional image is obtained using Optical Coherence Tomography (OCT) techniques.

15 Claims, 3 Drawing Sheets

(56) References Cited

U.S. PATENT DOCUMENTS

| | | |
|---|---|---|
| 7,252,662 B2 | 8/2007 | McArdle et al. |
| 7,798,641 B2 | 9/2010 | Bille |
| 7,844,425 B2 | 11/2010 | Bille et al. |
| 8,208,688 B2 | 6/2012 | Everett et al. |
| 2003/0063258 A1 | 4/2003 | Torii et al. |
| 2006/0028619 A1* | 2/2006 | Fujieda ............ A61B 3/1015 351/246 |
| 2006/0195076 A1 | 8/2006 | Blumenkranz et al. |
| 2006/0274269 A1 | 12/2006 | Koest |
| 2009/0137993 A1 | 5/2009 | Kurtz |
| 2009/0190093 A1 | 7/2009 | Tanassi et al. |
| 2011/0087324 A1 | 4/2011 | Salvati et al. |
| 2011/0202044 A1 | 8/2011 | Goldshleger et al. |
| 2011/0202046 A1* | 8/2011 | Angeley et al. ................ 606/6 |
| 2011/0208172 A1 | 8/2011 | Youssefi et al. |
| 2012/0133889 A1* | 5/2012 | Bergt .................. A61B 3/113 351/206 |
| 2013/0235343 A1* | 9/2013 | Hee .................. A61B 3/102 351/206 |
| 2014/0241605 A1* | 8/2014 | Izatt .................. G01B 11/2441 382/131 |

OTHER PUBLICATIONS

PCT International Search Report, Application No. PCT/US2013/035822, Apr. 9, 2013.

* cited by examiner

SYSTEM AND METHOD FOR CREATING A CUSTOMIZED ANATOMICAL MODEL OF AN EYE

This application claims the benefit of U.S. Provisional Patent Application Ser. No. 61/636,582, titled SYSTEM AND METHOD FOR CREATING A CUSTOMIZED ANATOMICAL MODEL OF AN EYE, filed Apr. 20, 2012. The entire contents of Application Ser. No. 61/636,582 are hereby incorporated by reference herein.

FIELD OF THE INVENTION

The present invention pertains generally to systems and methods for creating templates. More particularly, the present invention pertains to systems and methods for creating templates that are useful as a control reference for moving a laser beam's focal point during ophthalmic surgery. The present invention is particularly, but not exclusively, useful as a system and method for creating templates that will replicate the anatomical object that is to be altered during a laser ophthalmic surgery.

BACKGROUND OF THE INVENTION

It is axiomatic that any ophthalmic surgical procedure must be accomplished with great accuracy and precision. This is particularly so when a laser system will be used to cut or ablate tissue deep inside an eye. In such cases, it becomes particularly important that there is some operational base reference which can be established to control movements of the laser beam's focal point during a surgery.

Imaging devices, such as those that employ Optical Coherence Tomography (OCT) techniques, have been particularly helpful for providing information that is useful in performing ophthalmic laser surgeries. Nevertheless, OCT imaging techniques, alone, are not always able to provide the degree of precision that is required to establish a discernible and accurate base reference for the control of laser surgeries within the eye. For any number of reasons, an OCT image may lack the sharpness or clarity that is necessary or desired. In the specific case of ophthalmic surgeries, however, the eye itself can be helpful in overcoming these deficiencies.

The anatomy of an eye is well known. In particular, for the purpose of establishing a base reference, the eye's anatomy is unique because, unlike most other body parts, many of its structures are substantially symmetrical. Most importantly, the light refractive, optical elements of the eye are all aligned along a definable central axis, and they are arranged in a known anatomical order. It happens that the central axis can be easily identified for such an arrangement of optical elements, and it can be accurately defined by any of several standard techniques.

It is well known that the interface surfaces between different optical structures inside the eye (e.g. the interface surface between the anterior chamber and the anterior capsule of the crystalline lens) can be effectively imaged by OCT. Consequently, the location of an intersection between an interface surface and the central axis can also be accurately established by OCT. Moreover, due to their symmetry on the central axis, the size and extent of the various optical elements in the eye can also be predicted with great accuracy. As recognized by the present invention, such a replication of structural elements can be used, altogether or in part, to establish a base reference for use in an ophthalmic laser procedure.

In light of the above, it is an object of the present invention to provide a system and method that will establish a base reference inside an eye for controlling an ophthalmic laser procedure. Another object of the present invention is to provide a system and method for using OCT techniques to establish a base reference that results from an automated anatomical recognition of different optical elements in an eye (i.e. different refractive tissues) and the location of these elements (tissues). Still another object of the present invention is to provide a system and method for establishing a base reference inside an eye that is easy to assemble, is simple to use and is comparatively cost effective.

SUMMARY OF THE INVENTION

In accordance with the present invention, a system and method are provided for replicating anatomical features inside an eye. Specifically, this is done to create a template for identifying anatomical structures that can be used as a base reference for controlling a laser system during ophthalmic laser surgery (e.g. a capsulotomy) inside the eye.

As required for the present invention, a first step in the creation of a template involves the identification of a central ("z") axis for the eye. Structurally, this "z" axis needs to be identified such that the optical elements (i.e. light refractive structures) of the eye will be symmetrically aligned along the axis. Next, an OCT device is used to create a cross sectional image of the eye. Importantly, this image is created to include the "z" axis. Once the OCT cross sectional image has been created, and the central "z" axis has been incorporated into the image, various reference points are established along the central "z" axis. Specifically, based on the OCT image, each of the reference points is selected and located where an interface surface between adjacent optical elements in the eye intersects the central "z" axis. In this context, each reference point is specifically related to a particularly identified anatomical surface in the image. The result here is a plurality of contiguous lengths ($\Delta"z"_n$) along the "z" axis that are individually measured between adjacent reference points. These lengths will be anatomically recognized and can be measured with great accuracy. In essence, at this point a template based on the "z" axis has been created that can be used to replicate the optical elements of the eye.

A refinement for the present invention can be made by accounting for any tilt there might be between the central "z" axis and the optical elements of the eye. As noted above, the optical elements need to be symmetrically aligned along the central "z" axis. In accordance with the present invention, compensation for a tilt angle "Φ" can be accomplished in either of two ways. In order to compensate for a tilt angle "Φ" (in both ways of compensating for "Φ") it is first necessary to establish a base reference axis that is substantially oriented in a "z" direction. A base reference point is then located on the base reference axis. Importantly, the base reference point is located on an interface surface inside the eye (object).

For one methodology of the present invention, a first axis is identified that is substantially parallel to the base reference axis, and is at a distance "$d_1$" from the base reference axis. A first reference point is then located on the first axis where the first axis intersects the interface surface. The z-location of the first reference point is then compared with an expected z-location for the first reference point to determine a first differential ($\delta_z'$). Similarly, a second axis is identified that is also substantially parallel to the base reference axis, at a distance "$d_2$" from the base reference axis. A second reference point is then located on the second axis where the second axis intersects the interface surface. The z-location of the second reference point is then compared with an expected location for the second reference point to determine a second differential ($\delta_z''$). With this first methodology $\delta_z'$ and $\delta_z''$, along with a measurement of the angle between the respective planes identified by the first and second axes with the base reference axis (e.g. 90° for XZ and YZ planes), are used to measure an angle of tilt ($\Phi$) for the interface surface. The tilt angle $\Phi$ can then be used to refine the establishment of the central "z" axis.

In another methodology, after a base reference axis is established and a base reference point is located on an interface surface inside the eye (object), a circular path in traced on the interface surface at a distance "r" from the base reference axis. Variations in "z" along the path can then be measured to identify a differential ($\delta_z$) relative to a rotation angle ($\theta$) about the base reference axis. Specifically, in this case, $\delta_z$ is measured between a $z_{max}$ at $\theta_1$ and a $z_{min}$ at $\theta_2$. Then, using $\delta_z$, $\theta_1$ and $\theta_2$, the angle of tilt ($\Phi$) for the interface surface can be measured. Like the first methodology, the tilt angle $\Phi$ can then be used to refine the orientation of the central "z" axis.

A template with greater precision and accuracy can be created by verifying the location of previously selected reference points. To do this, at least one verification point is detected on the "z" axis in the OCT image. Like the original reference points, this verification point will be exactly located on the "z" axis at the intersection of an interface surface with the "z" axis. The location of the verification point in relation to the location of a previously selected reference point is then identified, and measurements are taken to confirm the anatomical identity of the surface that is associated with the reference point.

For an operational use of a template that has been created in accordance with the present invention, a replica of the anatomical surface of an optical element can be symmetrically traced between adjacent reference points on the "z" axis. In particular, the replica is based on the location of the selected reference point(s) and on information in the image. As a template, at least one selected reference point, together with the "z" axis, can then be used as a base reference for controlling a movement of a laser beam focal point relative to an identified surface. For example, a first reference point can be located on a posterior surface of an anterior capsule, and a second reference point can be located on the anterior surface of a posterior capsule. Using this template as a control reference, the focal point of the laser beam can then be moved between the anterior capsule and the posterior capsule to perform a capsulotomy.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
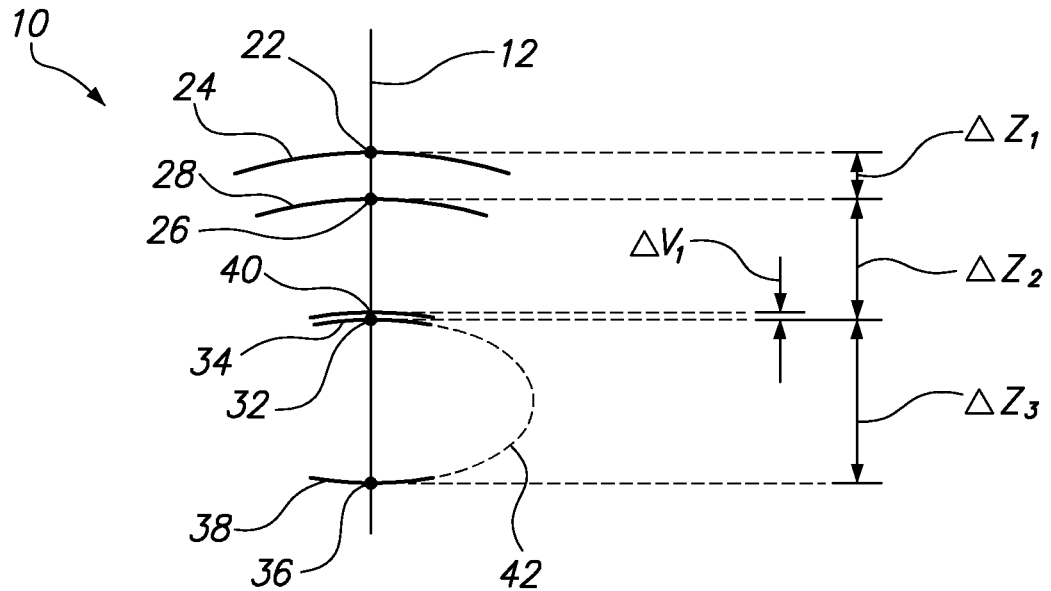
FIG. 1 is a line recognition template that has been created in accordance with the present invention.
Figure 2:
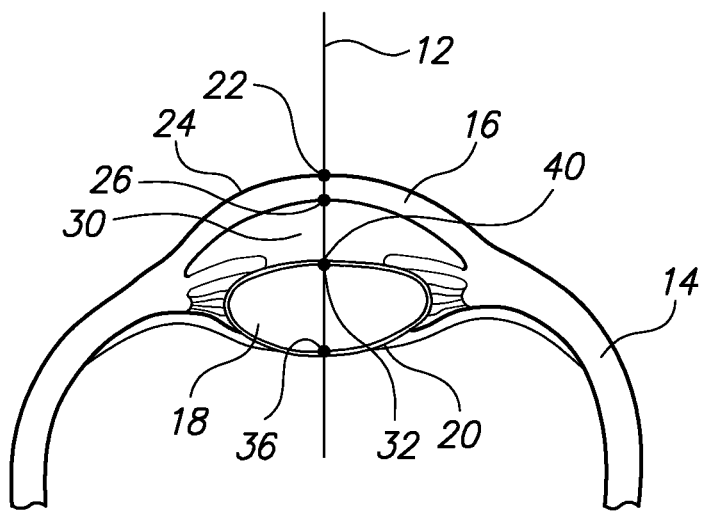
FIG. 2 is a representative cross sectional OCT image of the anterior portion of an eye.

Referring initially to FIG. 1, a line recognition template in accordance with the present invention is shown and is generally designated 10. As shown, the template 10 essentially includes a central "z" axis 12 that is unique for the present invention in several important respects. Most importantly, the axis 12 is selected primarily for the symmetry it establishes for optical elements of the eye 14, such as the cornea 16, the crystalline lens 18 and the capsular bag 20 of the lens 18. With reference to FIG. 2 it can be appreciated that each of these optical elements in the eye 14 will be axially symmetric relative to a properly oriented central "z" axis 12. Moreover, each of these optical elements is anatomically recognizable and they are all arranged in a set anatomical order along the axis 12.

In accordance with the present invention, the proper orientation of the axis 12 is initially established in relation to a cross sectional image of at least the anterior portion of the eye 14. As shown in FIG. 2, this image is preferably made using an imaging device of a type well known in the pertinent art that is capable of OCT imaging. Once the central "z" axis 12 has been properly oriented on the OCT image (see FIG. 2), dimensional references that correspond to optical features of the eye 14 are established along the axis 12.

By way of example, consider the reference point 22 on central "z" axis 12. With this reference point 22 in mind, it is well known that the anterior surface 24 of cornea 16 can be imaged using OCT techniques. In particular, from the perspective of the refractive differences of the adjacent media, and the capabilities of OCT imaging, the surface 24 can be identified as the interface surface between the environmental air and the cornea 16. Consequently, the intersection of this surface 24 with the axis 12 can be used to accurately set a location for the reference point 22 on the axis 12. These same considerations and capabilities can be used to accurately set other reference points.

Following from the above disclosure, reference point 26 can be identified and located on the central "z" axis 12 at the intersection of the interface surface 28 with the axis 12. In this case, surface 28 is the interface between the cornea 16 and the anterior chamber 30 of eye 14 (see FIG. 2). Further, the reference point 32 can be identified and located on the axis 12 at the intersection of an anterior interface surface 34 with the axis 12. In this case, the anterior interface surface 34 lies between the crystalline lens 18 and the capsular bag 20, in the anterior portion of the crystalline lens 18. Still further, the reference point 36 can be identified and located on the axis 12 at the intersection of posterior interface surface 38 with the axis 12. In this case, the posterior interface surface 38, in the posterior portion of the crystalline lens 18, lies between the crystalline lens 18 and the capsular bag 20.

Referring again to FIG. 1, it is to be appreciated that the template 10 is established with anatomically accurate dimensional information. Specifically, in this example, the length "$\Delta z_1$" effectively represents the thickness of cornea 16 along the axis 12 between reference point 22 and reference point 26. The measured length of "$\Delta z_1$" is then anatomically determined with reference to the OCT image of eye 14 shown in FIG. 2. The length "$\Delta z_2$" (i.e. the length along axis 12 across the anterior chamber 30 between reference point 26 and reference point 32) is similarly determined, as is the length "$\Delta z_3$" between reference points 32 and 36. Thus, the orientation of the central "z" axis 12, together with the placement of the reference points 22, 26, 32 and 36 on the axis 12 and their corresponding contiguous lengths "$\Delta z_1$", "$\Delta z_2$" and "$\Delta z_3$", collectively create the template 10. The result is a template 10 that can be superposed on an OCT image (see FIG. 3) and used as a control reference for ophthalmic surgical procedures, such as a capsulotomy.

For a refinement of the present invention, it is to be understood that a template 10 which is created in accordance with the above disclosure, can be verified for accuracy, if desired. To do so, a verification point 40 is selected. In this case, the verification point 40 shown in FIG. 1 is only exemplary, and it is taken to be the most anterior intersection of the capsular bag 20 with the central "z" axis 12. The corresponding verification distance "$\Delta v_1$" (i.e. the thickness of the capsular bag 20) can then be measured to determine whether the distance "$\Delta v_1$" and its location on the axis 12 will verify the accuracy of template 10.

In another aspect of the present invention, selected reference points can be used to trace the outline of optical elements in the eye 14. For example, in FIG. 1 a traced outline of the crystalline lens 18 is shown by the dotted line 42. As shown, the dotted line 42 represents extensions of the interface surfaces 34 and 38, between the reference points 32 and 36 that replicate the boundary of the crystalline lens 18. Again, this is only exemplary as it will be appreciated that similar extensions between other reference points can be made to replicate other optical elements in the eye 14.

Figure 3:
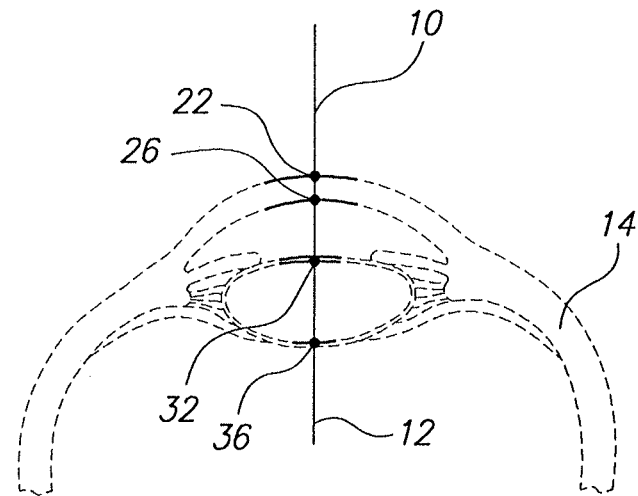
FIG. 3 shows the template of FIG. 1 superposed over a phantom drawing of the OCT image presented in FIG. 2.
Figure 4:
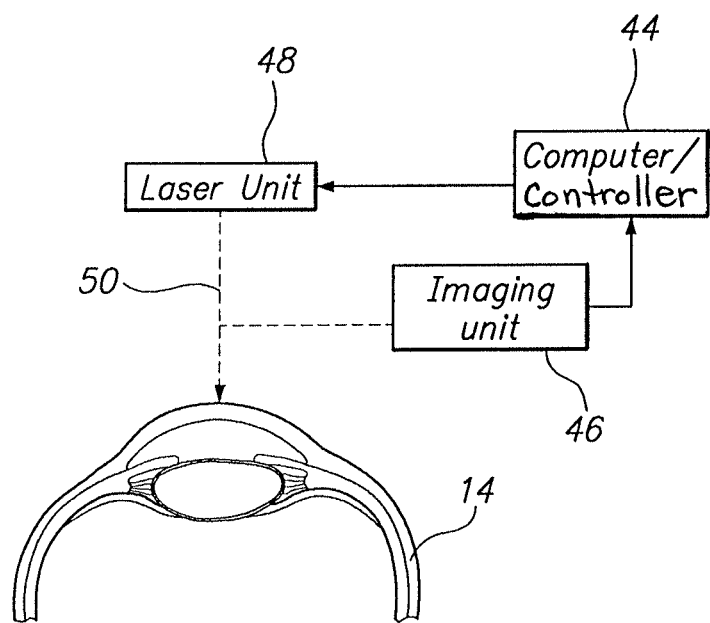
FIG. 4 is a schematic presentation of the system components that are used with the present invention for a laser ophthalmic surgical procedure.

In an operation of the present invention, the template 10 is superposed onto an OCT image of the eye 14 as shown in FIG. 3. As mentioned above, this is done to establish a base reference that can be used by the computer/controller 44 for laser control purposes. As envisioned for the present invention, the template 10 (i.e. FIG. 3) is based on images of the eye 14 obtained from the imaging unit 46. As indicated in FIG. 4, the computer/controller 44 can the effectively control the laser unit 48 to guide and control a laser beam 50 during an ophthalmic surgical operation in the eye 14.

Figure 5:
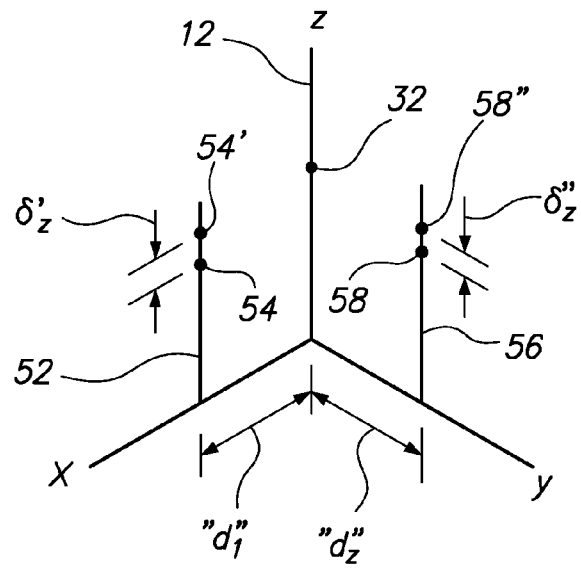
FIG. 5 is a geometric presentation of positional deviations related to a central axis of an eye, which are indicative of a "tilt" of the eye.

In another aspect of the present invention, the location and orientation of the central "z" axis 12 can be refined in accordance with either of two methodologies. For the first methodology, reference is directed to FIG. 5 where the reference point 32, on interface surface 34, is used as an example. In this example, the reference point 32 is shown located on the base central axis 12. An axis 52 is then identified that is substantially parallel to the base central axis 12, and is located at a distance "$d_1$" from the base central axis 12. Further, based on imaging techniques as disclosed above, a reference point 54 is located on the axis 52 that is actually located on the interface surface 34. The computer/controller 44 (FIG. 4) then compares the actual location of the reference point 54 with an expected location for the reference point 54' to determine a first differential ($\delta_z'$).

With further consideration of the first methodology, an axis 56 is identified which is also substantially parallel to the base central axis 12, and is located at a distance "$d_2$" from the base central axis 12. Further, a reference point 58 is located on the axis 56 which is also on the interface surface 34. As was done with reference point 54, the computer/controller 44 compares the location of the reference point 58 with an expected location for the reference point 58" to determine a second differential ($\delta_z''$). The computer/controller 44 then uses $\delta_z'$ and $\delta_z''$ to measure an angle of tilt ($\Phi$) for the interface surface 34, and incorporates the tilt angle $\Phi$ into its control over an operation of the laser unit 48.

Figure 6:
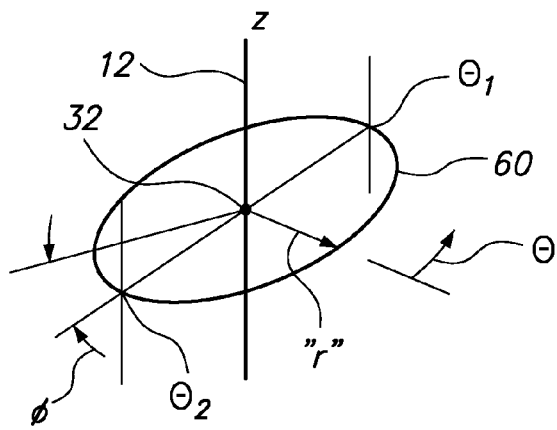
FIG. 6 is a trace of a circular path around a central axis of an eye that is indicative of a "tilt" of the eye.
Figure 7:
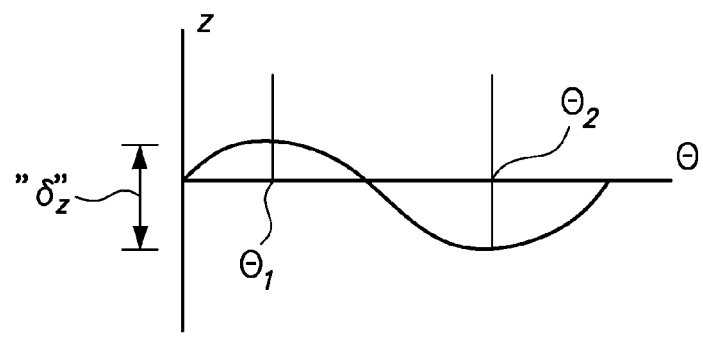
FIG. 7 is a graphical presentation of an angular "tilt" of the trace shown in FIG. 6.

For a second methodology that can be alternatively employed to refine the orientation and location of the base central axis 12, FIG. 6 indicates that a circular path 60 can be identified that encircles the base central axis 12. Importantly, the path 60 lies on an interface surface (e.g. interface surface 34). Thus, the reference point 32 will be located on the base central axis 12, with the path 60 on the interface surface 34 at a distance "r" from the base central axis 12. The computer/controller 44 is then used to measure variations in "z" along the path 60. Specifically, these variations are measured relative to a rotation angle ($\theta$) that is taken about the base central axis 12. The result of these measurements is shown in FIG. 7. As will be appreciated by the skilled artisan, the measurements from FIG. 7 can then be used by the computer/controller 44 to identify a differential ($\delta_z$) which is measured between a $z_{max}$ at $\theta_1$ and, 180° later, a $z_{min}$ at $\theta_2$. The computer/controller 44 then uses $\delta_z$, $\theta_1$ and $\theta_2$ to measure an angle of tilt ($\Phi$) for the interface surface 34, and incorporates the tilt angle $\Phi$ into its control over an operation of the laser unit 48.

While the particular System and Method for Creating a Customized Anatomical Model of an Eye as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for creating a line recognition template to replicate an object which comprises the steps of:
   aligning a plurality of reference points along a linear axis;
   establishing a base reference axis, wherein the base reference axis is oriented in a "z" direction;
   locating a base reference point on the base reference axis, wherein the base reference point is on an interface surface inside the object;
   tracing a circular path on the interface surface, wherein the path is at a distance "r" from the base reference axis;
   measuring variations in "z" along the path relative to a rotation angle ($\theta$) about the base reference axis to identify a differential ($\delta_z$), wherein $\delta_z$ is measured between a $z_{max}$ at $\theta_1$ and a $z_{min}$ at $\theta_2$;
   using $\delta_z$, $\theta_1$ and $\theta_2$ to measure an angle of tilt ($\phi$) for the linear axis;
   locating the reference points on the linear axis with anatomically measured contiguous lengths ($\Delta "z"_n$) along the linear axis between sequentially adjacent reference points; and
   tracing an axially-symmetric surface from selected reference points to create the template for replicating the object.

2. A method as recited in claim 1 wherein the locating step and the tracing step are based on a cross sectional image of the object.

3. A method as recited in claim 2 wherein the cross sectional image is obtained using techniques selected from a group comprising Optical Coherence Tomography (OCT), Scheimpflug, two-photon imaging and range finding.

4. A method as recited in claim 1 further comprises the steps of:
   identifying a first axis, wherein the first axis is substantially parallel to the base reference axis and is at a distance "$d_1$" from the base reference axis;
   locating a first reference point on the first axis, wherein the first reference point is located on the interface surface;
   comparing the location of the first reference point with an expected location for the first reference point to determine a first differential ($\delta_z'$);

identifying a second axis, wherein the second axis is substantially parallel to the base reference axis and is at a distance "$d_2$" from the base reference axis;

locating a second reference point on the second axis, wherein the second reference point is on the interface surface;

comparing the location of the second reference point with an expected location for the second reference point to determine a second differential ($\delta_z''$); and using $\delta_z'$ and $\delta_z''$ to measure verify the angle of tilt ($\phi$).

5. A method as recited in claim 1 further comprising the step of using at least one selected reference point, together with the axis, as a base reference for controlling a movement of a laser beam focal point relative to the axially-symmetric surface.

6. A method as recited in claim 5 wherein a first reference point is located on a posterior surface of an anterior capsule and a second reference point is located on an anterior surface of a posterior capsule, and the focal point of the laser beam is moved between the anterior capsule and the posterior capsule to perform a capsulotomy.

7. A method for replicating anatomical features inside an eye which comprises the steps of:

identifying a "z" axis for the eye;

determining a tilt angle $\phi$ for the "z" axis relative to a base reference axis;

locating a base reference point on the base reference axis, wherein the base reference point is on an interface surface inside the object;

tracing a circular path on the interface surface, wherein the path is at a distance "r" from the base reference axis;

measuring variations along the base reference axis relative to a rotation angle ($\theta$) about the base reference axis to identify a differential ($\delta$), wherein $\delta$ is measured between a $\delta_{max}$ at $\theta_1$ and a $\delta_{min}$ at $\theta_2$;

using $\delta$, $\theta_1$ and $\theta_2$ to measure the angle of tilt ($\phi$);

creating a cross sectional image of the eye, wherein the image includes the "z" axis;

establishing a plurality of reference points aligned in sequence along the "z" axis in the cross sectional image, wherein each reference point is respectively located where a surface shown in the image intersects the "z" axis;

relating each reference point to a particularly identified anatomical surface in the image;

measuring a plurality of contiguous lengths ($\Delta"z"_n$) along the "z" axis, wherein each length is individually measured between sequentially adjacent reference points; and tracing an axially-symmetric surface from selected reference points to create a template replicating anatomical features inside the eye.

8. A method as recited in claim 7 wherein the creating step is accomplished using an Optical Coherence Tomography (OCT) device.

9. A method as recited in claim 7 further comprising the step of tracing a replica of an anatomical surface, wherein the replica is based on the location of a selected reference point and information in the image.

10. A method as recited in claim 7 further comprising the step of using at least one selected reference point, together with the "z" axis, as a base reference for controlling a movement of a laser beam focal point relative to an identified surface.

11. A method as recited in claim 10 wherein a first reference point is located on a posterior surface of an anterior capsule and a second reference point is located on an anterior surface of a posterior capsule, and the focal point of the laser beam is moved between the anterior capsule and the posterior capsule to perform a capsulotomy.

12. A non-transitory, computer-readable medium having executable instructions stored thereon for use with a computer to create a line recognition template to replicate an object, the instructions comprising: aligning a plurality of reference points in sequence along a linear axis; establishing a base reference axis oriented in a "z" direction and locating a base reference point on the base reference axis at an interface surface inside the object; tracing a circular path on the interface surface at a distance "r" from the base reference axis, and measuring variations in "z" along the path relative to a rotation angle ($\theta$) about the base reference axis to identify a differential ($\delta_z$), wherein $\delta_z$ is measured between a $z_{max}$ at $\theta_1$ and a $z_{min}$ at $\theta_2$ and using $\delta_z$, $\theta_1$ and $\theta_2$ to measure an angle of tilt ($\phi$) for the linear axis; locating the aligned reference points with measured contiguous lengths ($\Delta"z"_n$) along the axis between sequentially adjacent reference points; and tracing an axially-symmetric surface from selected reference points for creating the template to replicate the object.

13. A medium as recited in claim 12 further comprising instructions for using at least one selected reference point, together with the axis, as a base reference for controlling a movement of a laser beam focal point relative to the axially-symmetric surface.

14. A medium as recited in claim 13 wherein a first reference point is located on a posterior surface of an anterior capsule and a second reference point is located on an anterior surface of a posterior capsule, and the focal point of the laser beam is moved between the anterior capsule and the posterior capsule to perform a capsulotomy.

15. A medium as recited in claim 12 wherein the program sections for locating and tracing are based on a cross sectional image of the object and the image is obtained using Optical Coherence Tomography (OCT) techniques.

* * * * *